US00PP27084P2

(12) United States Plant Patent
Oudolf

(10) Patent No.: US PP27,084 P2
(45) Date of Patent: Aug. 23, 2016

(54) *VERONICA* PLANT NAMED 'CANDIED CANDLE'

(50) Latin Name: ***Veronica spicata*×*Veronica longifolia***
Varietal Denomination: Candied Candle

(71) Applicant: Petrus Hendricus Oudolf, Hummelo (NL)

(72) Inventor: Petrus Hendricus Oudolf, Hummelo (NL)

(73) Assignee: Green Elite Collection B.V., Lisserbroek (NL)

( * ) Notice: Subject to any disclaimer, the term of this patent is extended or adjusted under 35 U.S.C. 154(b) by 99 days.

(21) Appl. No.: 14/120,666

(22) Filed: Jun. 14, 2014

(51) Int. Cl.
*A01H 5/02* (2006.01)

(52) U.S. Cl.
USPC ..... Plt./251

(58) Field of Classification Search
USPC ..... Plt./251
See application file for complete search history.

(56) References Cited

PUBLICATIONS

Morningsun Herb Farm—*Veronica* 'Candied Candle' retrieved from the Internet on Nov. 23, 2015—www.morningsunherbfarm.com/product_info.php?products_id=1188.*

* cited by examiner

*Primary Examiner* — Susan McCormick Ewoldt
(74) *Attorney, Agent, or Firm* — C. A. Whealy

(57) ABSTRACT

A new and distinct cultivar of *Veronica* plant named 'Candied Candle', characterized by its upright and relatively compact plant habit; freely branching habit; freely flowering habit; dark pink-colored flowers arranged on long racemes; and good garden performance.

3 Drawing Sheets

Botanical designation: *Veronica spicata*×*Veronica longifolia*.

Cultivar denomination: 'CANDIED CANDLE'.

BACKGROUND OF THE INVENTION

The present invention relates to a new and distinct *Veronica* plant, botanically known as *Veronica spicata*×*Veronica longifolia* and hereinafter referred to by the name 'Candied Candle'.

The new *Veronica* plant originated from a cross-pollination made by the Inventor during the summer of 2009 in Hummelo, The Netherlands, of an unnamed proprietary seedling selection of *Veronica spicata*, not patented, as the female, or seed, parent with an unnamed proprietary seedling selection of *Veronica longifolia*, not patented, as the male, or pollen, parent. The new *Veronica* plant was discovered and selected by the Inventor as a single flowering plant within the progeny of the stated cross-pollination in a controlled environment in Hummelo, The Netherlands during the summer of 2011.

Asexual reproduction of the new *Veronica* plant by vegetative softwood cuttings in Hummelo, The Netherlands, since the summer of 2011, has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype of the new *Veronica* plant may vary somewhat with variations in environmental conditions such as temperature and light intensity without, however, any variance in genotype.

The following traits have been repeatedly observed and are determined to be the unique characteristics of 'Candied Candle'. These characteristics in combination distinguish 'Candied Candle' as a new and distinct *Veronica* plant:

1. Upright and relatively compact plant habit.
2. Freely branching habit.
3. Freely flowering habit.
4. Dark pink-colored flowers arranged on long racemes.
5. Good garden performance.

Plants of the new *Veronica* differ from plants of the female parent selection primarily in flower color as plants of the female parent selection have light bluish pink-colored flowers. In addition, plants of the new *Veronica* are taller than plants of the female parent selection.

Plants of the new *Veronica* differ from plants of the male parent selection primarily in flower color as plants of the male parent selection have pink-colored flowers. In addition, plants of the new *Veronica* are shorter than plants of the male parent selection.

Plants of the new *Veronica* can be compared to plants of the *Veronica* 'Heidekind', not patented. In side-by-side comparisons conducted by the Inventor in Hummelo, The Netherlands, plants of the new *Veronica* differed from plants of 'Heidekind' in the following characteristics:

1. Plants of the new *Veronica* were taller than plants of 'Heidekind'.
2. Plants of the new *Veronica* were more freely branching than plants of 'Heidekind'.
3. Plants of the new *Veronica* and 'Heidekind' differed slightly in flower color.

BRIEF DESCRIPTION OF THE PHOTOGRAPHS

The accompanying colored photographs illustrate the overall appearance of the new *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet comprises a side perspective view of typical flowering stems of 'Candied Candle'.

The photograph on the second sheet is a close-up view of a typical leaf of 'Candied Candle'.

The photograph on the third sheet is a close-up view of typical inflorescences of 'Candied Candle'.

DETAILED BOTANICAL DESCRIPTION

Plants used for the aforementioned photographs and following description were grown during the late summer in an outdoor nursery in Rijpwetering, The Netherlands and under cultural practices typical of *Veronica* production. During the production of the plants, day temperatures ranged from 14° C. to 28° C. and night temperatures ranged from 4° C. to averaged 16° C. Plants were one year old when the photographs and description were taken. In the following description, color references are made to The Royal Horticultural Society Colour Chart, 2007 Edition, except where general terms of ordinary dictionary significance are used.

Botanical classification: *Veronica longifolia* cultivar Candied Candle.

Parentage:

*Female, or seed, parent*.—Unnamed proprietary seedling selection of *Veronica spicata*, not patented.

*Male, or pollen, parent*.—Unnamed proprietary seedling selection of *Veronica longifolia*, not patented.

Propagation:

*Type cutting*.—Vegetative softwood cuttings.

*Time to initiate roots, summer*.—About three weeks at temperatures about 18° C.

*Time to produce a rooted young plant, summer*.—About three months at temperatures about 18° C.

*Root description*.—Fine, moderately fibrous; greyish white in color.

*Rooting habit*.—Freely branching; dense.

Plant description:

*Growth and plant habit*.—Upright and relatively plant habit; broad inverted triangle; moderately vigorous growth habit; freely branching habit with about six lateral branches developing per plant.

*Plant height*.—About 51.3 cm.

*Plant width*.—About 41.6 cm.

*Lateral branch description*.—Length: About 41.1 cm. Diameter: About 3 mm. Internode length: About 5.8 cm. Strength: Strong. Texture: Densely pubescent. Color: Close to 144A.

Leaf description:

*Arrangement*.—Opposite, simple.

*Length*.—About 9.7 cm.

*Width*.—About 3.2 cm.

*Shape*.—Narrowly ovate to lanceolate.

*Apex*.—Acute.

*Base*.—Obtuse to truncate.

*Margin*.—Serrate.

*Texture, upper surface*.—Smooth, glabrous.

*Texture, lower surface*.—Moderately pubescent.

*Venation pattern*.—Pinnate.

*Color*.—Developing leaves, upper surface: Close to 143A to 143C. Developing leaves, lower surface: Close to 143C. Fully expanded leaves, upper surface: Close to between 137A and N137B; venation, close to 144A. Fully expanded leaves, lower surface: Close to 138B; venation, close to 144B to 144C.

*Petioles*.—Length: About 1.3 cm. Diameter: About 2 mm. Texture, upper and lower surfaces: Smooth, glabrous. Color, upper and lower surfaces: Close to 144B.

Flower description:

*Flower shape, arrangement and habit*.—Single campanulate flowers arranged on terminal and axillary racemes; flowers face mostly outwardly; freely flowering habit with about 360 flowers developing per inflorescence.

*Fragrance*.—Faintly fragrant; moderately sweet.

*Natural flowering season*.—Flowering continuous from late June to late September in The Netherlands.

*Flower longevity on the plant*.—About one week; flowers not persistent.

*Flower buds*.—Length: About 5 mm. Diameter: About 2 mm. Shape: Ovate. Color: Close to 63B.

*Inflorescence length*.—About 13.8 cm.

*Inflorescence diameter*.—About 2.4 cm.

*Flower diameter*.—About 7 mm.

*Flower depth* (*height*): About 9 mm.

*Petals*.—Arrangement: Four, fused about halfway to base. Length: About 7 mm. Width: About 3 mm. Shape: Oblanceolate. Apex: Broadly acute. Margin: Entire. Texture, upper and lower surfaces: Smooth, glabrous. Color: When opening, upper and lower surfaces: Close to 64C. Fully opened, upper and lower surfaces: Close to 64B to 64C; with development, color becoming closer to 64A to 64B.

*Calyx*.—Shape: Four sepals fused into a tube. Length: About 2 mm. Width: About 1 mm. Shape: Narrowly ovate. Apex: Acute. Texture, upper and lower surfaces: Smooth, glabrous. Color, upper and lower surfaces: Close to 137B; towards the base, close to 138B.

*Peduncles*.—Length: About 13.2 cm. Diameter: About 2.5 mm. Strength: Strong. Aspect: Primary racemes, mostly upright; secondary racemes, about 20° from vertical. Texture: Smooth, glabrous. Color: Close to 144B.

*Pedicels*.—Length: About 1.5 mm. Diameter: About 0.5 mm. Strength: Strong. Aspect: About 60° from the stem axis. Texture: Smooth, glabrous. Color: Close to between 146A and 147A.

*Reproductive organs*.—Stamens: Quantity per flower: Two. Filament length: About 8 mm. Filament color: Close to 71C to 71D. Anther shape: Elliptic. Anther length: About 1 mm. Anther color: Close to 71B. Pollen amount: Scarce to moderate. Pollen color: Close to 11C. Pistils: Quantity per flower: One. Pistil length: About 9 mm. Stigma shape: Clavate. Stigma color: Close to N79B. Style length: About 8 mm. Style color: Close to 72B. Ovary color: Close to 144D.

*Seeds and fruits*.—To date, seed and fruit production have not been observed on plants of the new *Veronica*.

Pathogen & pest resistance: Plants of the new *Veronica* have not been noted to be resistant to pathogens and pests common to *Veronica* plants.

Garden performance: Plants of the new *Veronica* have exhibited good tolerance to rain and wind, to tolerate high temperatures about 35° C. and to be hardy to USDA Hardiness Zone 4.

It is claimed:

1. A new and distinct *Veronica* plant named 'Candied Candle' as illustrated and described.

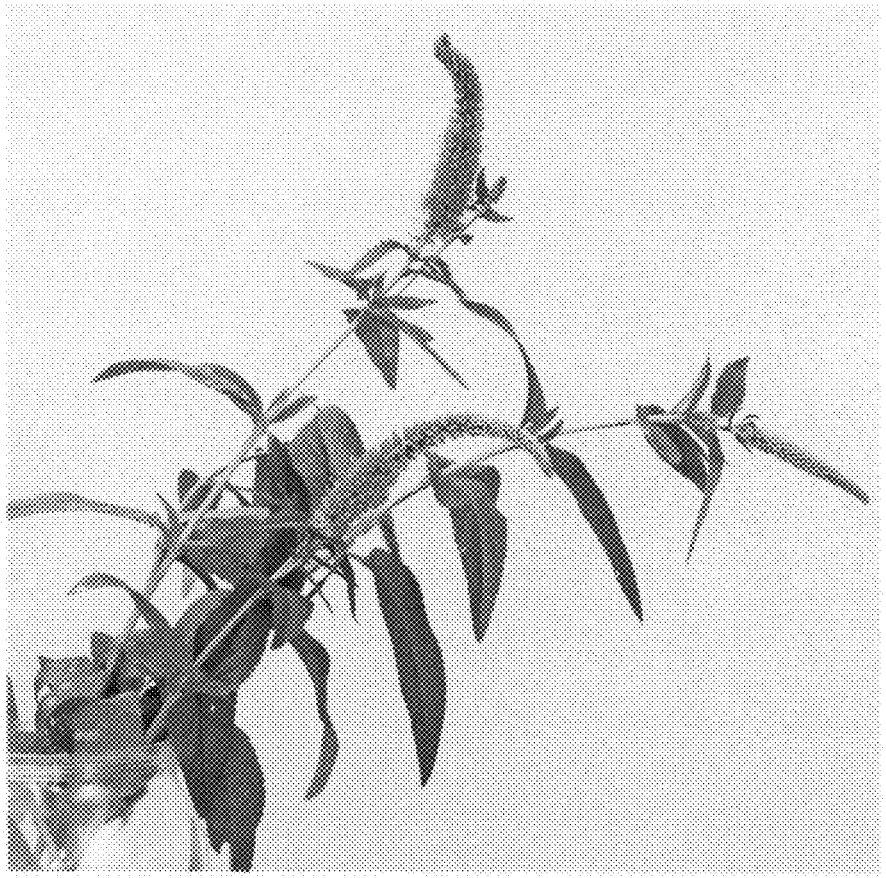

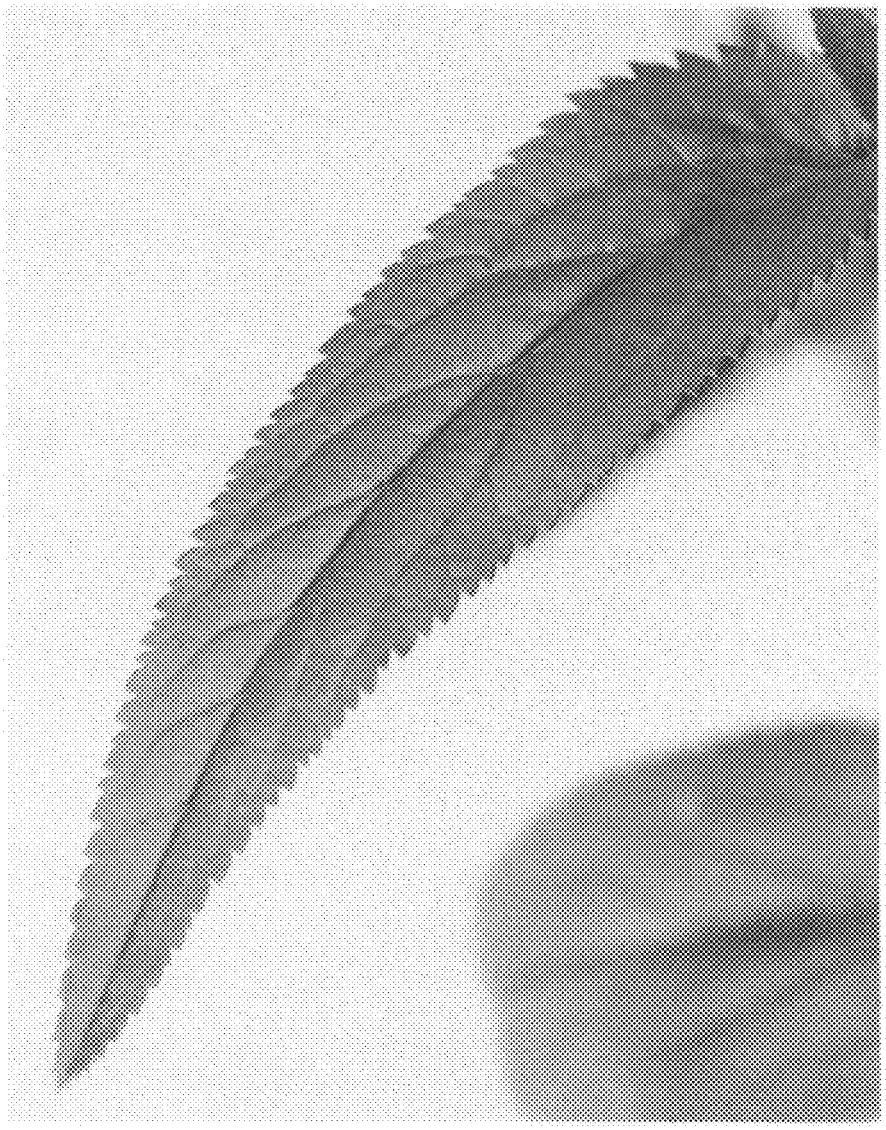

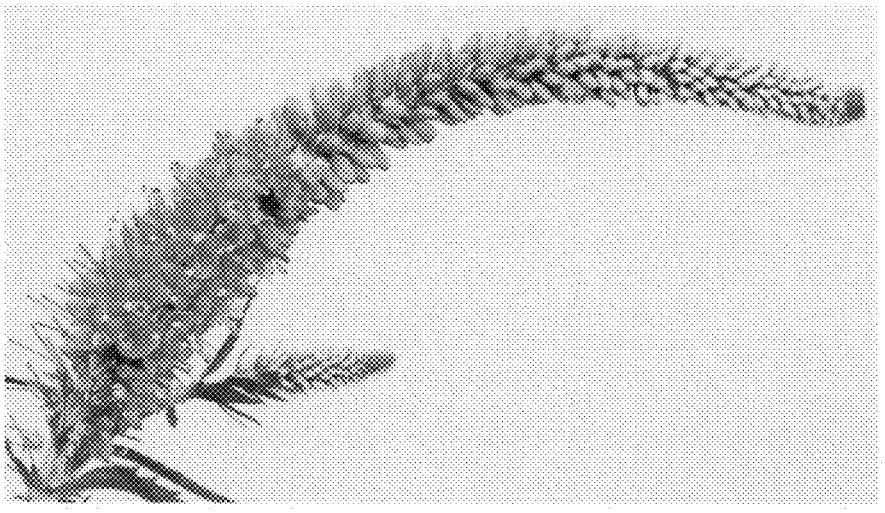

* * * * *